US00PP33050P3

(12) United States Plant Patent
Hogenboom

(10) Patent No.: US PP33,050 P3
(45) Date of Patent: May 11, 2021

(54) ***SPATHIPHYLLUM* PLANT NAMED 'SWEET ISABELLA'**

(50) Latin Name: ***Spathiphyllum* sp. Schott.**
Varietal Denomination: Sweet Isabella

(71) Applicant: P.C.M. Olsthoom Holding B. V., Honselersdijk (NL)

(72) Inventor: Niek Hogenboom, Honselersdijk (NL)

(73) Assignee: P.C.M. Olsthoorn Holding B. V., Honselersdijk (NL)

( * ) Notice: Subject to any disclaimer, the term of this patent is extended or adjusted under 35 U.S.C. 154(b) by 0 days.

(21) Appl. No.: 16/906,123

(22) Filed: Jun. 19, 2020

(65) Prior Publication Data

US 2021/0007258 P1 Jan. 7, 2021

(30) Foreign Application Priority Data

Jul. 5, 2019 (QZ) ..... PBR 2019/1330

(51) Int. Cl.
*A01H 5/02* (2018.01)
*A01H 6/12* (2018.01)

(52) U.S. Cl.
USPC ..... Plt./364
CPC ..... *A01H 6/12* (2018.05); *A01H 5/02* (2013.01)

(58) Field of Classification Search
USPC ..... Plt./364
CPC ..... A01H 6/00; A01H 5/02
See application file for complete search history.

*Primary Examiner* — Keith O. Robinson
(74) *Attorney, Agent, or Firm* — Samuel R. McCoy, Jr.

(57) ABSTRACT

'Sweet Isabella' is a new and distinctive variety of *Spathiphyllum* plant which is characterized by broad, dark green foliage, strong and rigid petioles, the lack of pollen production, and the stability of all characteristics from generation to generation. The new variety is typically produced as an indoor ornamental plant.

3 Drawing Sheets

Latin name of the genus and species: The Latin name of the genus and species of the novel variety disclosed herein is *Spathiphyllum* sp. Schott.

Variety denomination: The inventive variety of *Spathiphyllum* disclosed herein has been given the variety denomination 'Sweet Isabella'.

CROSS REFERENCE TO RELATED APPLICATIONS

This application claims priority to the Community Plant Variety Rights application number 2019/1330, filed Jul. 5, 2019, which is herein incorporated by reference.

BACKGROUND OF THE INVENTION

Parentage: The new cultivar is a seedling selection which resulted from the controlled pollination of the proprietary seed parent, *Spathiphyllum* sp. '09076-2' (not patented), and the proprietary pollen parent, *Spathiphyllum* sp. '09076-4' (not patented). Both parents are developed and owned by the inventor and were never commercially released. Said cross was performed by the inventor at a commercial greenhouse in Honselersdijk, The Netherlands during the winter of 2015. After approximately one and a half years of evaluating the seedlings that resulted from said cross, the new cultivar was selected in the summer of 2016 due to its broad, dark green foliage and lack of pollen production. The new cultivar was given the breeder denomination 'Sweet Isabella'.

Asexual Reproduction: Asexual reproduction of 'Sweet Isabella', by way of meristematic tissue culture, was first performed in 2017 at a commercial laboratory in Honselersdijk, the Netherlands. Four successive generations so produced have shown that the unique features of the instant cultivar are stable and reproduced true to type.

SUMMARY OF THE INVENTION

The cultivar 'Sweet Isabella' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Spathiphyllum* cultivar 'Sweet Isabella'. These traits, in combination, distinguish 'Sweet Isabella' as a new and distinct cultivar.

1. *Spathiphyllum* 'Sweet Isabella' exhibits broad, dark green foliage; and
2. *Spathiphyllum* 'Sweet Isabella' exhibits strong, rigid petioles; and
3. *Spathiphyllum* 'Sweet Isabella' exhibits a lack of pollen production.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
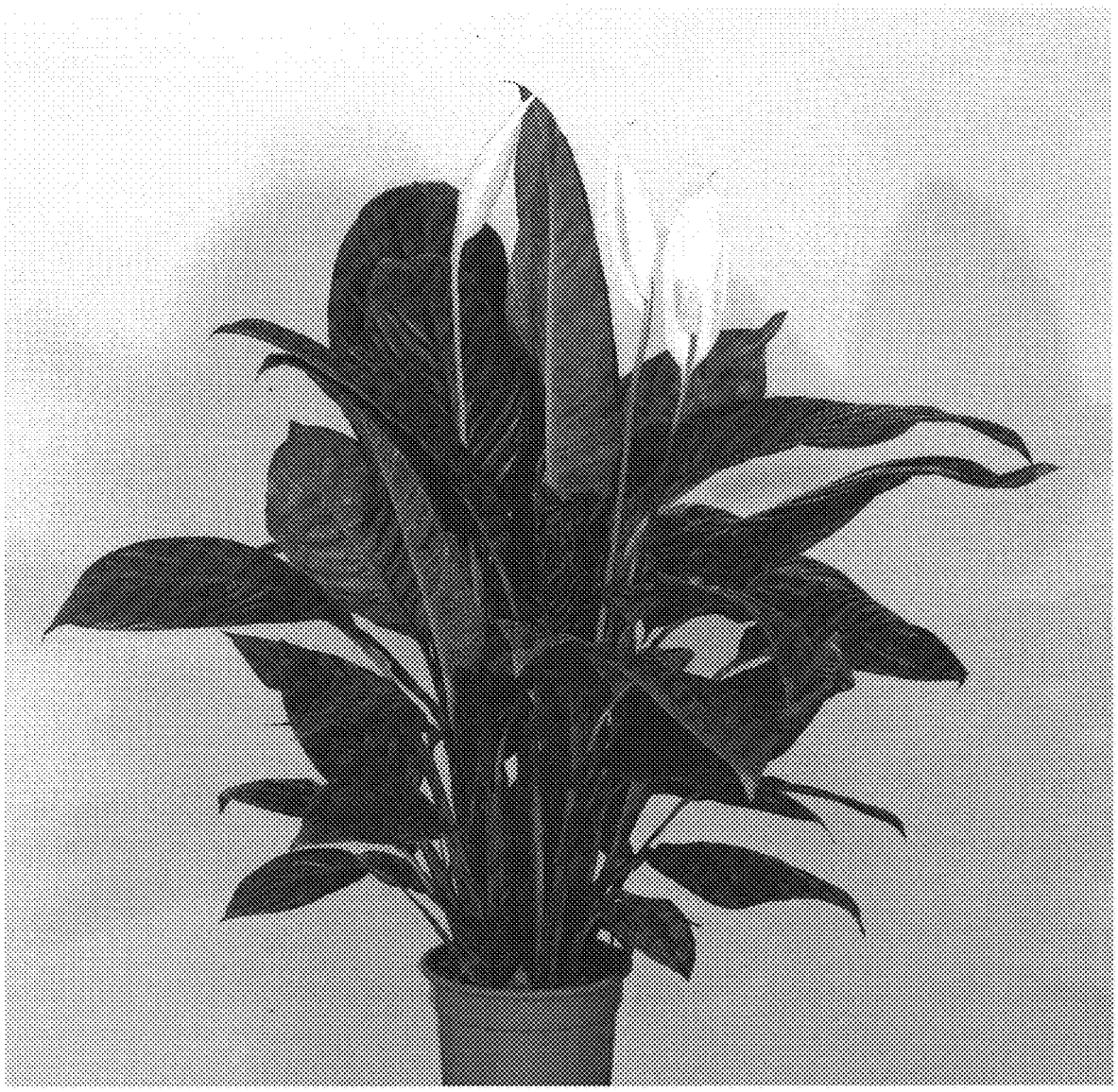
FIG. 1 shows, as nearly true as it is reasonably possible to make the same in color illustrations of this type, the typical foliage and growth characteristics of the new cultivar, 'Sweet Isabella'. The plant shown is approximately 12 months old from a rooted cutting, potted into a 17 cm nursery pot, grown in a climate-controlled greenhouse in Roelofarendsveen, the Netherlands.
Figure 2:
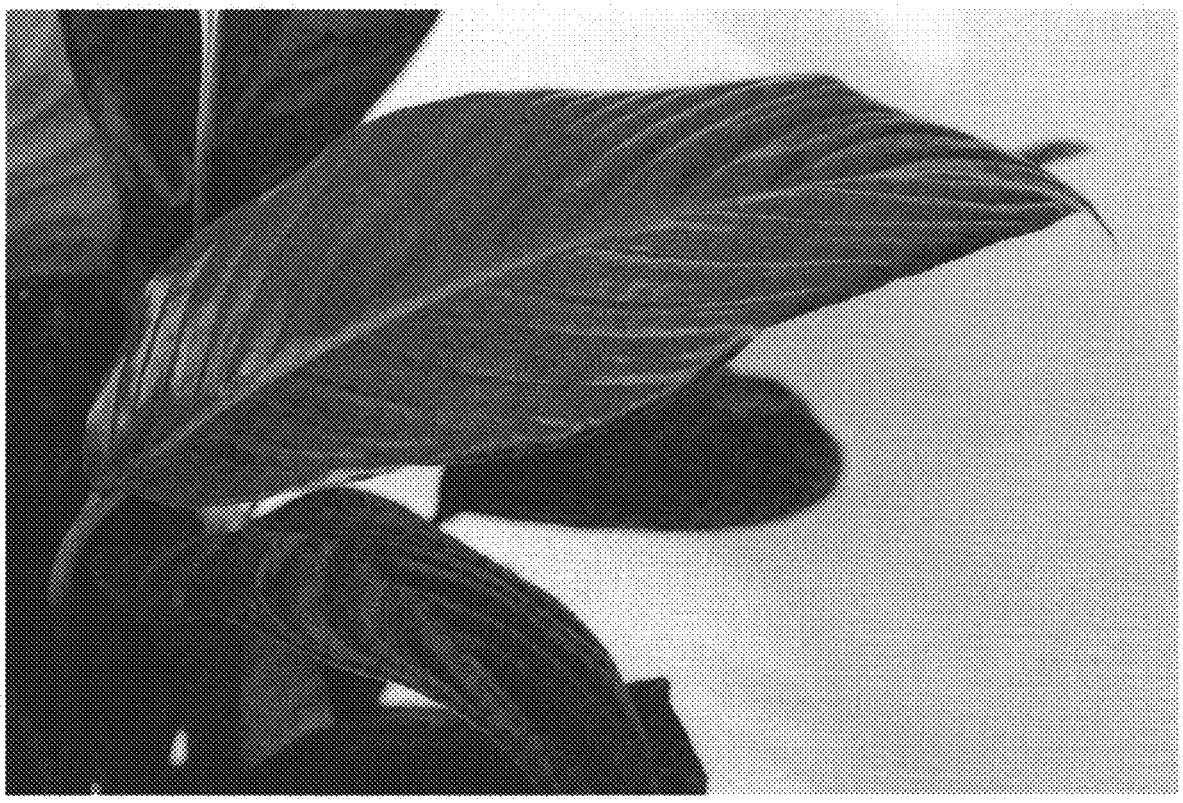
FIG. 2 shows, as nearly true as it is reasonably possible to make the same in color illustrations of this type, the typical foliage of the plant in FIG. 1.
Figure 3:
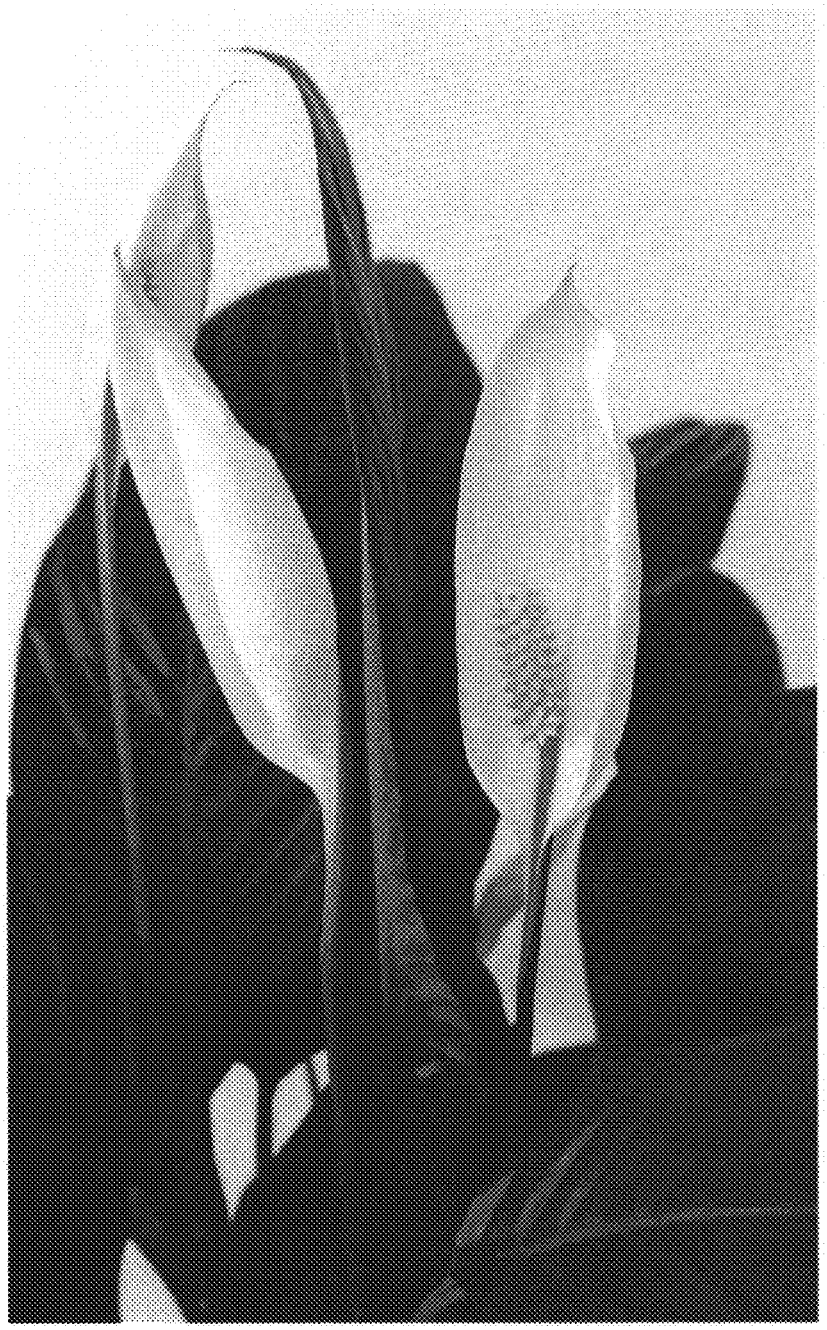
FIG. 3 shows, as nearly true as it is reasonably possible to make the same in color illustrations of this type, the typical flower of the plant in FIG. 1.

The following observations and measurements made in January of 2020 describe averages from a sample set of six specimens of 1 year old 'Sweet Isabella' plants grown in 17 cm nursery containers at commercial greenhouse in Roelofarendsveen, the Netherlands. Plants were produced using conventional greenhouse production protocols for *Spathiphyllum* which consisted of 5,000 to 8,000 lux of light, regular overhead irrigation, fertilizer applications at an Electrical Conductivity level of 2.3. No chemical pest and disease control measures were taken. No photoperiodic treatments or artificial light was given to the plants.

Those skilled in the art will appreciate that certain characteristics will vary with older or, conversely, with younger plants. 'Sweet Isabella' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'Sweet Isabella' and comparisons with the parents and the most similar variety of common knowledge are provided below.

General plant description:

*Growth habit*.—Clump forming; broad spreading to upright with foliage arising directly from the base of each clump.

*Plant profile*.—Broad obovate to near globular with inflorescences carried within the foliage.

*Height*.—78.0 cm in height, to the highest leaf; 77.0 cm to top of highest spathe.

*Width*.—Average 95.0 cm in width.

*Growth rate*.—Moderately fast to fast growing.

*Plant vigor*.—Highly vigorous.

*Propagation*.—Method — Meristematic tissue culture. Time to initiate roots — Approximately 28 days to initiate roots at approximately 21 degrees Centigrade. Crop time — Approximately 35 weeks to produce a well-rooted 13 cm container from a rooted cutting.

*Environmental tolerances*.—Moderately high tolerance to rain and wind; tolerant of temperatures ranging from 5 to 40 degrees Celsius. Cold hardy to USDA Hardiness Zone 10.

*Pest resistance and susceptibility*.—Plants have not been observed to be any more or less susceptible or resistant to pathogens and pests common to *Spathiphyllum*.

Root system: Moderately fibrous, not fleshy; moderately dense.

Stems:

*Branching characteristics*.—Clumping plant with leaves emerging directly from the base of the plant; no lateral branching.

Foliage:

*Arrangement*.—Alternate; equitant.

*Division*.—Simple.

*Attachment*.—Petiolate.

*Quantity of leaves per shoot*.—Average of 5.

*Quantity of shoots per plant*.—Average of 11.

*Quantity of leaves per plant*.—Approximately 55.

*Lamina*.—Shape — Broad ovate to broad elliptic. Apex — Apiculate to aristate. Base — Short attenuate. Aspect — Slightly carinate, slightly reflexed with leaf tip curled downward at an average angle of approximately 60 degrees to the balance of the laminar surface. Attitude — Upright and slightly outward. Dimensions — 36.8 cm long and 18.3 cm wide. Margin — Entire; slightly undulate. Texture and luster, adaxial surface — Smooth, glabrous, and glossy. Texture and luster, abaxial surface — Smooth, glabrous, and moderately glossy. Juvenile color, adaxial surface — Green, nearest to in between RHS NN137B and 141B. Juvenile color, abaxial surface — Green, nearest to RHS 138A. Mature color, adaxial surface — Nearest to in between green and yellow-green, RHS NN137A and N147A. Mature color, abaxial surface — Yellow-green, nearest to RHS 147B. Venation — Vein pattern — Pinnate. Vein color, adaxial surface — Green, nearest to RHS 143A. Vein color, abaxial surface — Yellow-green, nearest to RHS 145A.

*Petiole, excluding geniculum*.—Length — Approximately 39.2 cm. Width — Approximately 0.55 cm at the geniculum and 1.0 cm at the base. Color, adaxial surface — Green, nearest to RHS 137B. Color, abaxial surface — Green, nearest to a mixture of RHS 137B and 137C. Texture and luster — Smooth, glabrous, and very slightly glossy. Strength — Strong. Geniculum — Length — Approximately 5.5 cm. Width — Approximately 0.75 cm. Texture and Luster — Smooth, glabrous and matte. Color — Green, nearest to a mixture of RHS 138A and 138B. Petiole wings — Length — Approximately 27.0 cm. Width — Approximately 1.1 cm. Color, adaxial surface — Green, nearest to RHS 138B. Color, abaxial surface — Yellow-green, nearest to RHS 144A.

Inflorescence:

*Type*.—Spathe.

*Arrangement*.—Peduncles arise directly from the base of the plant with spathes carried at or below the foliar plane.

*Attitude*.—Near vertical.

*Dimensions*.—19.0 cm long, excluding the peduncle, and 5.4 cm wide; spathe is 3.1 cm deep.

*Flowering habit*.—Continuous.

*Quantity of spathes per plant*.—On average 6 fully open spathes, in good condition.

*Natural flowering season*.—Autumn into spring in the Netherlands, with occasional flowering in summer.

*Time to flowering*.—24 weeks from planting.

*Fragrance*.—Faint, sweet and pleasant (typical *Spathiphyllum* scent).

*Self-cleaning or persistent*.—Persistent.

*Flower longevity*.—Flowers stay in good condition approximately 3 weeks on the plant.

*Peduncle*.—Attitude — Near vertical. Length — 65.1 cm. Diameter — 0.6 cm. Strength — Strong. Texture and luster — Smooth, glabrous and very slightly glossy. Color — Yellow-green, nearest to RHS 144A.

Spathe:

*Attitude*.—Near vertical.

*Aspect*.—Moderately to strongly concave.

*Length*.—Approximately 19.0 cm.

*Width*.—Approximately 5.4 cm.

*Depth*.—2.4 cm.

*Shape*.—Elliptic to ovate.

*Margin*.—Entire; very slightly undulate.

*Apex*.—Apiculate.

*Base*.—Long attenuate.

*Texture, inner and outer surfaces*.—Glabrous, slightly coriaceous.

*Luster, inner and outer surfaces*.—Inner surface is very slightly glossy; outer surface is moderately glossy.

*Color*.—Inner surface, when opening — White, nearest to RHS 155C, and tipped yellow-green, nearest to RHS 144B. Outer surface, when opening — White, nearest to RHS NN155A, and tipped yellow-green, nearest to a mixture of RHS 144A, 144B and 144C; main vein is also yellow-green, nearest to a mixture of RHS 144A, 144B and 144C. Inner surface, at maturity — White, nearest to RHS 155C, and tipped yellow-green, nearest to RHS 144B; main vein is green-white, nearest to a mixture of RHS 157A and 157B. Outer surface, at maturity — White, nearest to RHS NN155A, and tipped yellow-green, nearest to a mixture of RHS 144A and 144B; main vein is also yellow-green, nearest to a mixture of RHS 144A and 144B.

Spadix:

*Attitude*.—At an average angle of 15 degrees to the peduncle.

*Shape*.—Oblong, columnar.

*Apex*.—Obtuse.

*Base*.—Obtuse.

*Length*.—Approximately 4.8 cm.

*Width*.—Approximately 1.6 cm.

*Color*.—When opening — Yellow-white, nearest to RHS 158C. Mature — Greyed-yellow, nearest to RHS 162D.

*Flowers*.—General — Flowers are greatly diminished, to the point of being largely indistinguishable and immeasurable. Quantity of flowers per spadix — Approximately 100. Arrangement — Spirally placed on spadix. Shape — Rounded. Diameter — Approximately 0.4 cm. Height — Approximately 0.3 cm.

Reproductive organs:

*General*.—Reproductive organs are greatly diminished, to the point of being largely indistinguishable and immeasurable.

*Anthers*.—Color — Yellow-white, nearest to RHS 158B.

*Pollen, amount*.—No pollen detected.

*Stigma*.—Quantity — 1. Shape — Conical. Dimensions — 0.3 cm tall and 0.2 cm in diameter. Color — Greyed-yellow, nearest to RHS 162D.

*Ovary color*.—Greyed-yellow, nearest to RHS 162D.

Seed and fruit: Seed production has not been observed.

COMPARISONS WITH THE PARENT

Plants of the new cultivar 'Sweet Isabella' may be distinguished from the seed parent, *Spathiphyllum* sp. '09076-2' (not patented), by the following combination of characteristics:

1. 'Sweet Isabella' does not produce pollen, whereas the seed parent does produce pollen.

Plants of the new cultivar 'Sweet Isabella' may be distinguished from the pollen parent, *Spathiphyllum* sp. '09076-4' (not patented), by the following combination of characteristics:

1. 'Sweet Isabella' does not produce pollen, whereas the pollen parent does produce pollen.

COMPARISONS WITH THE MOST SIMILAR VARIETY OF COMMON KNOWLEDGE

Plants of the new cultivar 'Sweet Isabella' may be distinguished from the commercial variety *Spathiphyllum* 'Sweet Catalina' (for which a United States Patent application is being filed concurrently with the instant application) by the following combination of characteristics:

1. 'Sweet Isabella' exhibits larger spathes than those of 'Sweet Catalina'.
2. 'Sweet Isabella' exhibits larger foliage than that of 'Sweet Catalina'.
3. 'Sweet Isabella' is more vigorous when compared to 'Sweet Catalina'.

That which is claimed is:

1. A new and distinct variety of *Spathiphyllum* plant named 'Sweet Isabella', substantially as described and illustrated herein.

* * * * *